(12) United States Patent
Alexander et al.

(10) Patent No.: US 9,968,346 B2
(45) Date of Patent: May 15, 2018

(54) SYSTEMS, TOOLS, AND METHODS FOR TREATMENTS OF PELVIC CONDITIONS

(75) Inventors: James A. Alexander, Excelsior, MN (US); Chaouki A. Khamis, Edina, MN (US); Thomas O. Viker, Arden Hills, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 22 days.

(21) Appl. No.: 13/876,034

(22) PCT Filed: Sep. 29, 2011

(86) PCT No.: PCT/US2011/053938
§ 371 (c)(1),
(2), (4) Date: Mar. 26, 2013

(87) PCT Pub. No.: WO2012/050961
PCT Pub. Date: Apr. 19, 2012

(65) Prior Publication Data
US 2013/0225936 A1    Aug. 29, 2013

Related U.S. Application Data

(60) Provisional application No. 61/387,751, filed on Sep. 29, 2010, provisional application No. 61/502,694, (Continued)

(51) Int. Cl.
*A61B 17/02* (2006.01)
*A61B 1/303* (2006.01)
(Continued)

(52) U.S. Cl.
CPC .............. *A61B 17/02* (2013.01); *A61B 1/303* (2013.01); *A61B 1/32* (2013.01); *A61B 17/0206* (2013.01);
(Continued)

(58) Field of Classification Search
CPC . A61B 17/02; A61B 17/0206; A61B 17/0293; A61B 17/42; A61B 17/44; A61B 2017/0293; A61B 1/32; A61B 1/303
(Continued)

(56) References Cited

U.S. PATENT DOCUMENTS 202,813 A    4/1878 Hall
447,761 A *  3/1891 Clough .................. 600/224
(Continued)

FOREIGN PATENT DOCUMENTS

GB    2 424 585       10/2006
WO    WO2002/078552   10/2002
(Continued)

OTHER PUBLICATIONS

Tyco Healthcare, "IVS Tunneller," ICS/IUGA Symp. (2001).
(Continued)

*Primary Examiner* — Tatiana Nobrega
*Assistant Examiner* — Marcela I Shirsat
(74) *Attorney, Agent, or Firm* — Brake Hughes Bellermann LLP

(57) ABSTRACT

Described are surgical procedure systems, devices, tools, and methods, useful for treating pelvic conditions in a male or female, involving an expansion member. The invention relates to an expansion member that includes a proximal end, a distal end, a length extending from the proximal end to the distal end, two longitudinal blades extending in the length direction, and a connector connecting the blades. The connector allows movement of the blades to increase or decrease a distance between the blades at the distal end.

17 Claims, 6 Drawing Sheets

Related U.S. Application Data filed on Jun. 29, 2011, provisional application No. 61/515,685, filed on Aug. 5, 2011.

(51) Int. Cl.
| | |
|---|---|
| *A61B 1/32* | (2006.01) |
| *A61B 17/44* | (2006.01) |
| *A61B 17/42* | (2006.01) |
| *A61B 90/00* | (2016.01) |

(52) U.S. Cl.
CPC .......... *A61B 17/0293* (2013.01); *A61B 17/42* (2013.01); *A61B 17/44* (2013.01); *A61B 2090/3614* (2016.02)

(58) Field of Classification Search
USPC ............... 606/119, 108, 197, 198, 213, 135, 606/191–193; 600/220, 249, 184–200, 600/1–8, 29–32, 35, 38–40, 235, 241
See application file for complete search history.

(56) References Cited

U.S. PATENT DOCUMENTS

| | | | |
|---|---|---|---|
| 3,749,088 A * | 7/1973 | Kohlmann | 600/215 |
| 4,010,740 A | 3/1977 | Littorin | |
| 4,432,351 A * | 2/1984 | Hoary | 600/220 |
| 4,562,832 A * | 1/1986 | Wilder et al. | 600/223 |
| 4,597,030 A * | 6/1986 | Brody | A61B 1/07 362/572 |
| 4,834,067 A | 5/1989 | Block | |
| 5,112,344 A | 5/1992 | Petros | |
| 5,337,736 A | 8/1994 | Reddy | |
| 5,611,515 A | 3/1997 | Benderev et al. | |
| 5,683,349 A | 11/1997 | Makower et al. | |
| 5,785,648 A * | 7/1998 | Min | 600/206 |
| 5,842,478 A | 12/1998 | Benderev et al. | |
| 5,860,425 A | 1/1999 | Benderev et al. | |
| 5,899,909 A | 5/1999 | Claren et al. | |
| 5,944,732 A | 8/1999 | Raulerson et al. | |
| 6,039,686 A | 3/2000 | Kovac | |
| 6,354,995 B1 | 3/2002 | Hoffman et al. | |
| 6,432,048 B1 * | 8/2002 | Francois | A61B 1/303 600/186 |
| 6,450,952 B1 * | 9/2002 | Rioux et al. | 600/223 |
| 6,641,525 B2 | 11/2003 | Rocheleau et al. | |
| 6,648,921 B2 | 11/2003 | Anderson et al. | |
| 6,691,711 B2 | 2/2004 | Raz et al. | |
| 7,025,063 B2 | 4/2006 | Snitkin et al. | |
| 7,303,525 B2 | 12/2007 | Watwschke et al. | |
| 7,347,812 B2 | 3/2008 | Mellier | |
| 7,351,197 B2 | 4/2008 | Montpetit et al. | |
| 7,500,945 B2 | 3/2009 | Cox et al. | |
| 8,517,914 B2 | 8/2013 | Anderson et al. | |
| 8,827,902 B2 * | 9/2014 | Dietze, Jr. | A61B 17/0206 600/201 |
| 2002/0147382 A1 | 10/2002 | Neisz et al. | |
| 2004/0054260 A1 * | 3/2004 | Klaassen et al. | 600/220 |
| 2004/0143163 A1 | 7/2004 | Palmer et al. | |
| 2006/0205995 A1 | 9/2006 | Browning | |
| 2007/0043264 A1 | 2/2007 | Gillis et al. | |
| 2010/0298630 A1 | 11/2010 | Wignall | |
| 2011/0021869 A1 * | 1/2011 | Cholhan | 600/37 |
| 2012/0016185 A1 | 1/2012 | Sherts et al. | |

FOREIGN PATENT DOCUMENTS

| | | |
|---|---|---|
| WO | WO2007/097994 | 8/2007 |
| WO | WO2007/149348 | 12/2007 |
| WO | WO2007/149555 | 12/2007 |
| WO | WO2008/057261 | 5/2008 |
| WO | WO2011/082350 | 7/2011 |

OTHER PUBLICATIONS

Tyco Healthcare, "IVS Tunneller," ICS/IUGA Symp. (2002).

Winters, et al "Abdominal Sacral Colpopexy and Abdominal Enterocele Repair in the Management of Vaginal Vault Prolapse," Urology 56 (Suppl 6A) 55-63 (2000).

Paraiso et al, "Laparoscopic Surgery for Enterocele, Vaginal Apex Prolapse and Rectocele," Int Urogynecol J (1999).

\* cited by examiner

SYSTEMS, TOOLS, AND METHODS FOR TREATMENTS OF PELVIC CONDITIONS

PRIORITY CLAIM

This application claims the benefit from International No. PCT/US2011/053938, which was granted an International filing date of Sep. 29, 2011, which in turn claims priority under 35 USC § 119(e) from U.S. Provisional Patent Application having U.S. Ser. No. 61/502,694, filed Jun. 29, 2011, entitled "SYSTEMS, IMPLANTS, TOOLS, AND METHODS FOR TREATMENTS OF PELVIC CONDITIONS," U.S. Ser. No. 61/387,751, filed Sep. 29, 2010, entitled "SYSTEMS, IMPLANTS, TOOLS, AND METHODS FOR TREATMENTS OF PELVIC CONDITIONS," and U.S. Ser. No. 61/515,685, filed Aug. 5, 2011, entitled "SYSTEMS, IMPLANTS, TOOLS, AND METHODS FOR TREATMENT OF PELVIC CONDITIONS", which applications are incorporated herein by reference in their entireties.

FIELD OF THE INVENTION

The invention relates generally to systems, tools, and related methods for treating pelvic conditions including but not limited to prolapse conditions, for example by transvaginal sacral colpopexy procedures.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Urinary incontinence can be characterized by the loss or diminution in the ability to maintain the urethral sphincter closed as the bladder fills with urine. Male or female stress urinary incontinence (SUI) generally occurs when the patient is physically stressed. Other pelvic floor disorders include cystocele, rectocele, enterocele, and prolapse such as anal, uterine and vaginal vault prolapse. Pelvic disorders such as these can result from weakness or damage to normal pelvic support systems.

In its severest forms, vaginal vault prolapse can result in the distension of the vaginal apex outside of the vagina. Vaginal vault prolapse and enterocele represent challenging forms of pelvic disorders for surgeons. These procedures often involve lengthy surgical procedure times. Abdominal sacralcolpopexy (SCP) is considered to be an especially efficacious treatment, but it can be complicated and is generally considered invasive.

SUMMARY

Devices, systems, and methods as described can be used to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, hysterectomies and the like.

Certain described embodiments of devices and methods involve the use of a retractor or "expansion member" adapted to provide port access and guidance to a surgical site. These embodiments involve placement of an elongate expansion member through a body orifice or incision and to a surgical site, to create an access space from the exterior of the patient to the surgical site. The expansion member is useful to retract tissue, create an access space, and allow surgical instruments such as sharp tools to safely access the surgical site. Certain of these described embodiments relate generally to various means, devices, and techniques for providing a clear view of a surgical site in a region of a sacrum and nearby anatomy, through a vaginal incision. In several examples, this is provided by way of a device that can be inserted into a vaginal incision and then used to expand or dilate tissue.

In described examples, desired retraction functionality is provided by a device that can be changed in size, shape, or dimension, to contact and then move, expand, or dilate (e.g., retract) tissue. An expansion member may include two or more pieces (e.g., longitudinal panels or blades) that are optionally hinged or connected and able to move laterally or longitudinally relative to each other. The pieces can be moveable relative to each other in a manner that allows the pieces to define a space (access space) therebetween, the space or a portion thereof being capable of being varied in dimension, e.g., "expandable." In specific embodiments, the device can be inserted into a vaginal incision and then expanded, dilated, manipulated, or otherwise used for tissue retraction to create a working space and allowing access between the vaginal introitus and the vaginal apex, a posterior location of a pelvic region, or a region of sacral anatomy. Certain preferred versions of these tools can include distal end functionality to add efficiency to a surgical procedure, e.g., distal end functionality useful during a transvaginal sacral colpopexy, such as a lighting feature, an anchor driving feature, an optical feature that allows viewing of the surgical site, a laser-centerline indicator, suction, irrigation, or a dissection device.

In one aspect, the invention relates to an expansion member that includes a proximal end, a distal end, a length extending from the proximal end to the distal end, two longitudinal blades extending in the length direction, and a connector connecting the blades. The connector allows movement of the blades to increase or decrease a distance between the blades at the distal end.

In another aspect, the invention relates to methods of transvaginally performing pelvic surgery to support a vaginal apex. The methods include: providing an expansion member as described herein, inserting the distal end through a vagina introitus, and using the expansion member to provide access to a region of sacral anatomy.

See also Applicant's co-pending PCT patent application number PCT/US2011/053938, entitled "SYSTEMS, TOOLS, AND METHODS FOR TREATMENTS OF PELVIC CONDITIONS," filed on Sep. 29, 2011, the entirety of which is incorporated herein by reference.

DETAILED DESCRIPTION

Figure 1A:
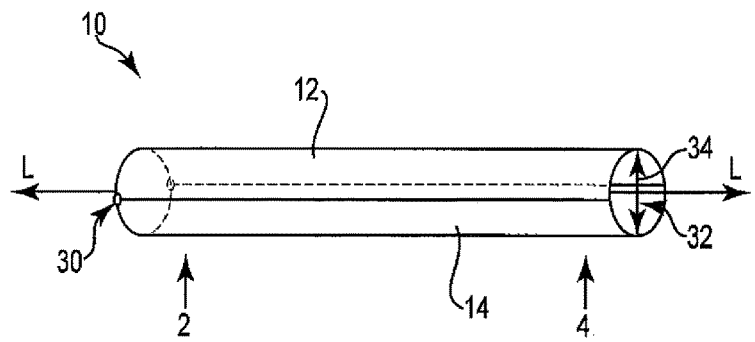
FIGS. 1A, 1B, and 1C are side views of an embodiment of an expansion member.

Pelvic disorders include cystocele, rectocele, enterocele, and uterine and vaginal vault prolapse, urinary and anal incontinence, among others, in male and female patients. These disorders typically result from weakness or damage to normal pelvic support systems. The most common etiologies include childbearing, removal of the uterus, connective tissue defects, prolonged heavy physical labor and postmenopausal atrophy.

Vaginal vault prolapse is the distension of the vaginal apex, in some cases to a configuration outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons.

Vaginal vault prolapse is often associated with a rectocele, cystocele, or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

Sling procedures are surgical methods that place a sling to stabilize or support the bladder neck or urethra. They are typically used to treat incontinence. There are a variety of different sling procedures. Slings used for pubovaginal procedures differ in the type of materials, size and shape, anchoring methods, and anchor placement. Examples of sling procedures are disclosed in U.S. Pat. Nos. 5,112,344; 5,611,515; 5,842,478; 5,860,425; 5,899,909; 6,039,686, 6,042,534 and 6,110,101.

A sacral colpopexy is a procedure for providing vaginal vault suspension. It may be performed through an abdominal incision, a vaginal incision, or laparoscopically. Typically, this procedure is accompanied by an abdominal enterocele repair and cul-de-sac obliteration. A sacral colpopexy entails suspension (by use of an implant such as a strip of mesh) of the vaginal cuff to a region of sacral anatomy such as the sacrum (bone itself), a nearby sacrospinous ligament, uterosacral ligament, or anterior longitudinal ligament at the sacral promontory. An implant such as a synthetic mesh can be carefully customized or assembled into a special shape by the surgeon. According to some procedures, a surgeon manually cuts a sheet of the mesh and stitches elements of the mesh to form the special shape. The literature reports surgeons suturing mesh material into various T-shaped articles. See Winters et al., "Abdominal Sacral Colpopexy and Abdominal Enterocele Repair in the Management of Vaginal Vault Prolapse," Urology 56 (Suppl 6A) (2000): 55-63; and Paraiso et al, "Laparoscopic Surgery for Enterocele, Vaginal Apex Prolapse and Rectocele," Int Urogynecol J (1999).

In some SCP procedures that also involve a hysterectomy, an implant can attach to posterior vaginal tissue remaining after removal of the uterus and cervix, and also to anatomy to support the vaginal tissue at or around the sacrum such as to uterosacral ligaments, the sacrum itself, a sacrospinous ligament, or anterior longitudinal ligament at the sacral promontory (i.e., to a component of the sacral anatomy).

As used herein, the term "anchor" refers non-specifically to any structure that can connect an implant to tissue of a pelvic region. The tissue may be bone or a soft tissue such as a muscle, fascia, ligament, tendon, or the like. The anchor may be any known or future-developed structure useful to connect an implant to such tissue, including but not limited to a clamp; a suture; a soft tissue anchor such as a self-fixating tip; a bone anchor; a screw, spiral, helical anchor, or coil; or any structure useful to connect an implant to soft tissue or bone of a pelvic region.

Embodiments of expansion members can include multiple elongate blades (portions, pieces, panels, sections, segments, or the like) that extend longitudinally from a proximal end of each blade to a distal end of each blade, also between a proximal end of the expansion member and a distal end of the expansion member. The blades are optionally connected or connectable, e.g., by a connector, in a manner that allows relative movement of the two blades to alter a dimension of an access space defined by the blades, e.g., laterally. The blades can be connected, for example, to allow movement of the blades at the distal end, to allow a distance or space between the blades at the distal end to be made bigger or smaller. A connection of two blades can be a rigid mechanical connection that may include a hinge, a joint, or a swivel, directly connecting one blade to the other, or that connects two blades to common structure such as a frame. Alternate connectors can be of a less rigid or a non-rigid material, such as a flexible film, fabric, membrane, mesh, web, or any other mechanism that allows movement of a blade relative to the other blade.

A blade is a generally elongate, substantially rigid member that makes up an operative and structural piece of the expansion member. Alternate terms for a "blade" may include a "piece," "section," "segment," or "panel" constituent of an expansion member. A blade can be substantially flat or can exhibit a curved cross-sectional profile. One or more longitudinal edges can be straight or curved, extending longitudinally between a proximal end and a distal end of each blade. A blade can be made of a substantially rigid material such as a plastic or other polymer, metal, or other material useful for a surgical tool or device. The length of each blade can be as desired for an expected application of the expansion member. For certain embodiments of expansion members, a length of a blade can be sufficient to extend between a space exterior to a vaginal introitus and a region of sacral anatomy, when placed transvaginally. A width (or height) of a blade can be sufficient to create an access space between two or more blades of an expansion member as described herein. A blade may generally have a length that is greater in dimension that a width, and have a thickness dimension that is a fraction of an inch, e.g., 1 to 3 millimeters.

The expansion member includes at least two blades, optionally three, four, or even more blades, with each blade connected to an adjacent blade, along a hinge, connecting a longitudinal edge of one blade to a longitudinal edge of the adjacent blade.

The blades, or opposing or adjacent portions of blades, such as opposing or adjacent distal end portions of two blades, can move relative to each other to increase (or decrease) a distance or dimension between the blades or portions of blades. The blades may optionally be connected to handles at the proximal end, which can be used to move (e.g., open and close) the blades.

Each blade may exhibit a flat cross section, or a curved cross section such that a cross sectional space defined between opposing or adjacent blades of an expansion member (an access space) includes a circular, semi-circular, or a segment or multiple cross-sectional semi- or partial-circular portions.

Optionally, an opening (e.g., slot or channel) may extend along an inferior (bottom or lower) side of an expansion member, along a superior (top or upper) side of the expansion member, or along both inferior and superior sides. An opening may extend from the distal end, toward the proximal end, partially along the length of the expansion member. Alternately, an opening can extend the entire length between the distal end and the proximal end. An opening can allow desired access to tissue at a distal end of the expansion member during a surgical procedure. In certain embodiments, a flexible and optionally elastic connector, membrane, mesh, film, or other connective material can be located to span or cover the opening, while still allowing desired movement between the blades. The expansion member may not fully enclose an access space along the length or around a circumference of the device, between the distal and proximal ends, but may leave one portion or side (along the partial or total length of the expansion member) open, giving access to tissue. For example, a "bottom" side of an expansion member may lack structure, leaving an opening along a length of the device to allow access to a peritoneum and fixation of mesh at locations of exposed tissue, e.g., by suturing.

Other features can include a taper (e.g., a narrowing of the shape from the proximal end to the distal end; ribs for retention within the patient; sacral mating geometry (shaping of the distal end) or materials (e.g., conforming materials such as "tissue wipers") at the far end or tips of one or more segments of a tool; a longitudinal (parallel or approximately parallel to a longitudinal axis or longitudinal dimension of the expansion member) (straight or curved) hinge between moveable segments; selective expansion (adjustment of a width dimension) of an expansion member at different locations along a length of an expansion member, e.g., to match the anatomy of a patient; selective adjustment of a length dimension of an expansion member, e.g., to match the anatomy of a patient; and locks or ratchets to maintain one or more selectively set dimensions of an expansion member.

Also optionally, an expansion member can include a locking mechanism that will hold the blades in a desired configuration while the expansion member is being used and is located within a patient, to cause the expansion member to remain in the desired configuration and expand tissue to create the access space.

An expansion member can be used to allow surgical items such as tools, sutures, implants, or components thereof, or other objects (e.g., sharp objects) to be passed safely through an access space of the expansion member from an external location to an internal surgical site.

In certain embodiments an expansion member can be useful for transvaginally accessing a female pelvic anatomy, especially a female pelvic anatomy, to access tissue of the posterior pelvic region such as to perform a transvaginal sacral colpopexy (TSCP) procedure. An expansion member can have a length to allow such access when the expansion member is placed transvaginally, e.g., a length to allow a distal end of the expansion member to access pelvic tissue while a proximal end of the expansion member extends through a vaginal opening to a location external to the patient. The proximal end of the expansion member remains external to the patient during use to allow a surgeon or other user to access and manipulate the proximal end and access a surgical site at the distal end, through the access space of the expansion member. Exemplary lengths between a proximal end of an expansion member and a distal end of the expansion member may be in the range from 13 to 18 centimeters, especially for use in a female patient to transvaginally access a posterior location of a pelvic region such as a region of sacral anatomy.

The diameter of the expansion member (defining the access space) can be useful to allow the tool to be inserted and placed in a patient (e.g., transvaginally) with reduced trauma. Optionally, as described elsewhere herein, a diameter of the expansion member, or the size of the access space, can be variable, such as by being expandable after placement within a patient, to allow increased and expanded access to tissue at a surgical site.

An expansion member can include one or more functional features within the access space or at the distal end (or distal region) such as one or more of a dissection feature (a mechanical dissection using a sharp blade, or hydrodissection), a blunt dissection feature, a viewing (visualization) feature, a feature for illumination of a surgical location, a feature for fluid delivery at a surgical location, a feature for irrigation at a surgical location, a feature for suction at a surgical location, and a feature for placing anchors (bone anchors, soft tissue anchors such as a self-fixating tip, sutures, etc.) into a desired target tissue at a surgical location such as a coil driver. An expansion member may include an optional laser at the proximal end that can shine along a centerline of the expansion member, within the access space.

An expansion member or portion or component thereof can be constructed of any known or compatible materials, including polymers or metals. A blade, handle, connector, mechanical hinge, swivel, or joint component, or other rigid structure can be constructed of metal or a rigid polymeric material such as a polypropylene, polyacrylate, polycarbonate, stainless steel, steel, polyester, or other similar material. A non-rigid material such as a non-rigid connector may be made of a non-rigid, flexible, pliable material suitable for use in a surgical instrument, such as a flexible, pliable polymer, mesh, film, woven or non-woven fabric, etc. Examples include natural or synthetic rubber, silicone, polyurethane, polyolefin (e.g., polypropylene, polyethylene), and the like.

Figure 1B:
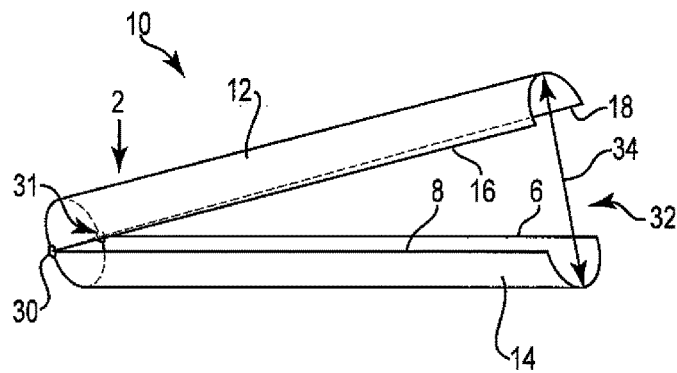
Figure 1C:
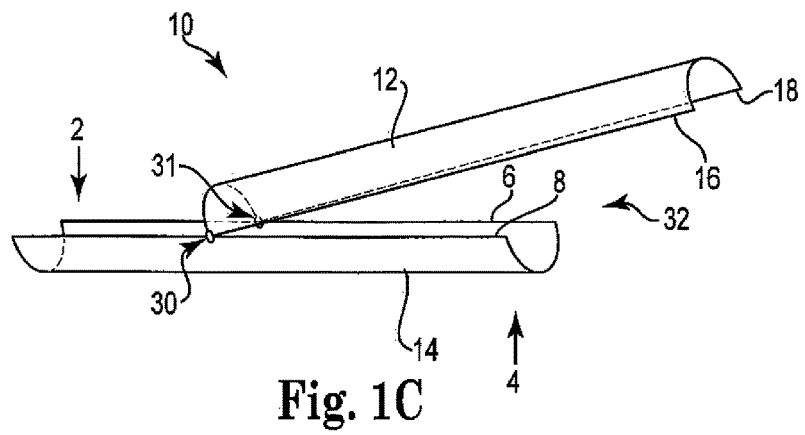

Referring to FIGS. 1A, 1B, 1C, and 1D, retractor or expansion member 10 includes proximal end 2, distal end 4, and two longitudinal blades, 12, and 14. Expansion member 10 is configured for use during a surgical procedure to provide access to a surgical site or anatomy, e.g. transvaginal access to a region of sacral anatomy. Blade 12 is a top blade having a curved cross-sectional profile, and blade 14 is a bottom blade having an opposing curved cross-sectional profile (see FIG. 1D). Blades 12 and 14 are connected at proximal end 2 by hinges 30 and 31, which allow blades 12 and 14 to move between a closed configuration wherein top blade 12 and bottom blade 14 are engaged along their longitudinal edges (see FIGS. 1A and 1D), and an open configuration wherein top blade 12 and bottom blade 14 are spread apart by pivoting at proximal end 2 about hinges 30 and 31 (see FIGS. 1B and 1C). Optionally, hinges 30 and 31 can allow for sliding movement between top blade 12 and bottom blade 14. As shown at FIG. 1C, hinges 30 and 31 can be slidably connected to upper edges 8 and 6 of bottom blade 14, allowing upper blade 12 to slide in a distal or proximal direction relative to bottom blade 14. Access space 32 is the longitudinal space between blades 12 and 14, including longitudinal axis "L." Width 34 is measured between top blade 12 and bottom blade 14, and can be increased or decreased by movement of blades 12 and 14 about hinges 30 and 31.

Figure 1D:
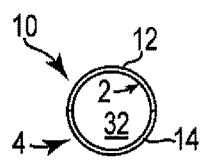
FIG. 1D is an end view of an embodiment of an expansion member.

In a closed configuration, as illustrated at FIGS. 1A and 1D (end view) hinges 30 and 31 are closed and blades 12 and 14 are folded together along their respective edges 8 and 6, and 16 and 18. From that closed configuration, blades 12 and 14 can be separated along the length of expansion member 10 by rotating blades 12 and 14 about hinges 30 and 31. In the open configuration, as illustrated at FIGS. 1B and 1C, hinges 30 and 31 are opened and blades 12 and 14 are spread by pivoting at hinges 30 and 31. The size of access space 32 is increased.

In use, expansion member 10 can be placed in the closed or folded configuration by folding blades 12 and 14 together as shown at FIGS. 1A and 1D. In the closed configuration, expansion member 10 can be introduced through an incision or body orifice (e.g., into a vaginal introitus and through a transvaginal incision at a posterior of vaginal tissue). Upon placement into a body orifice, expansion member 10 can be converted to an open configuration by moving blades 12 and 14 away from each other, increasing the size of access space 32 between the separated blades. The spread-apart blades retract tissue by pushing tissue away from longitudinal axis L.

For use in a transvaginal procedure to access tissue in a region of a sacrum, a surgeon can insert expansion member 10 transvaginally, with expansion member 10 in the closed configuration. Proximal end 2 remains external to the patient and distal end 4 passes transvaginally to a location at a posterior pelvic region, e.g., at a surgical location at a region of sacral anatomy. During or after insertion, expansion member 10 can be opened by spreading blades 12 and 14 away from each other in a pivoting motion about hinges 30 and 31, to increase the size of access space 32 between the blades. Optionally and preferably expansion member 10 (i.e., blades 12 and 14) can be locked into the open (expanded) configuration while the surgical procedure is performed. Top blade 12 can optionally be moved in a distal direction by movement of sliding hinges 30 and 31 along upper edges 8 and 6. As one specific use in a transvaginal procedure such as a transvaginal sacrocolpopexy, one or more of blades 12 and 14 may be used to push bowel away from a surgical location at a sacral promontory, as expansion member 10 is advanced transvaginally toward the sacral promontory. After the surgical procedure is completed, expansion member 10 can be returned to a closed position and then removed from the patient.

Figure 2A:
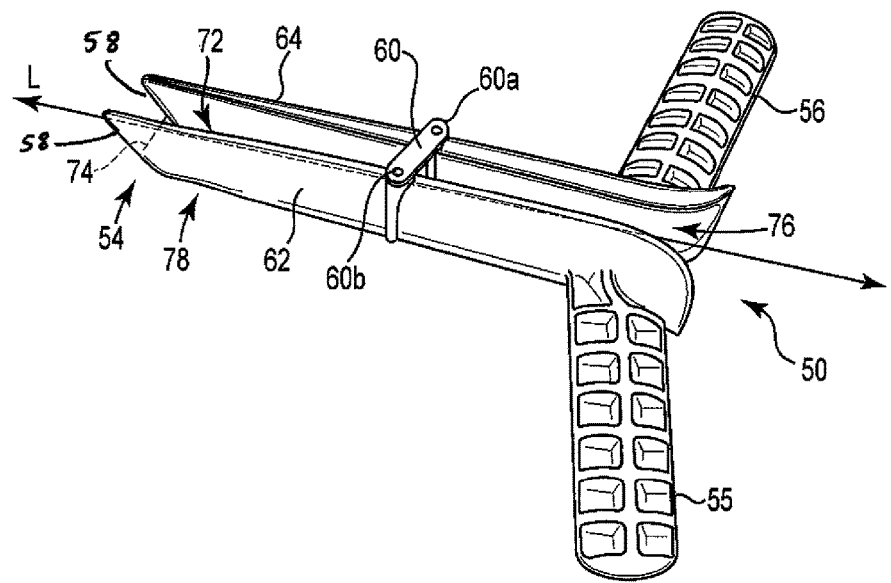
FIGS. 2A and 2B are top perspective views of an embodiment of an expansion member.
Figure 2B:
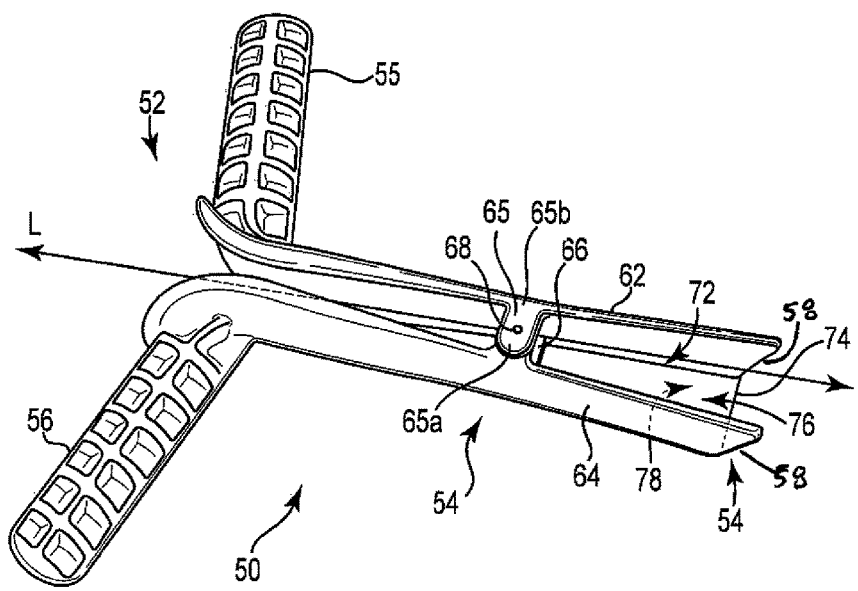

FIGS. 2A and 2B show two versions of expansion members 50. Each expansion member 50 includes proximal end 52, distal end 54, two longitudinal blades 62 and 64, and handles 55 and 56. Connectors (60 and 65, at FIGS. 2A and 2B) (or lateral connectors) connect blades 62 and 64 at a location between proximal end 52 and distal end 54, allowing lateral movement of the handles and blades at proximal end 52, and a resultant opposite lateral movement of the blades at distal end 54.

The connector (e.g., 60, 61, 65, 66, or the like) can be any type of connector able to connect the blades and allow lateral movement of the blades at the distal end (with opposite movement at the proximal end) as desired. Because a connector located along a length of the expansion member away from the proximal end can become located within a patient and in contact with tissue during use, the connector can preferably be of a relatively small size and profile, and not involve unduly exposed, extended, protruding, or sharp or angled features that could contact internal tissue of a patient. Exemplary connectors can include a single hinge at a center location along a length of a connector (see FIG. 2B); two or more hinges, one at each end of a solid length of a connector (see FIG. 2A); or no hinges but a continuous bar, scaffold, or other connecting member connected at each of two opposing ends to one of the two blades, in which case the connector can deflect or bend to allow relative movement of the opposed blades.

Still referring to FIGS. 2A and 2B, expansion member 50 is configured for use during a surgical procedure to provide access to a surgical site or anatomy, e.g., transvaginal access to a region of sacral anatomy. Blade 62 is a side blade having a curved cross-sectional profile at proximal end 52, gradually changing along the length into a relatively straight cross-sectional profile at distal end 54. Blade 64 is a side blade having an opposing curved cross-sectional profile at proximal end 52, gradually changing along the length into a relatively straight cross-sectional profile at distal end 54. Access space 76 is the longitudinal interior space between blades 62 and 64, including longitudinal axis "L." Optionally and as illustrated, expansion member 50 includes top and bottom longitudinal openings (slots, or channels) 72 and 78 extending longitudinally along the full length of expansion member 50, between opposing top and bottom edges of blades 62 and 64. Width 74 is measured between blades 62 and 64 at a location at the distal end (e.g., as shown at FIGS. 2A and 2B). Width 74 can be increased or decreased by movement of handles 55 and 56 in opposite directions.

Also illustrated as an optional feature of an expansion member, distal end 54 includes distal edge 58, situated at an angle relative to longitudinal axis L, when expansion member 50 is viewed from a side. As illustrated, distal edge 58 is angled or slanted relative to longitudinal axis L in a direction that allows edge 58 to align with a slant of pelvic anatomy at a posterior region of a patient's pelvis, such as at a region of sacral anatomy, while expansion member 50 is installed transvaginally. To achieve this angle, a length between the proximal and distal ends of the expansion member is longer at the top (superior side) of the expansion member and is relatively shorter at the bottom (inferior side) of the expansion member (when viewed from a side).

Referring now specifically to FIG. 2A, expansion member 50 includes connectors 60 and 61 (60 on top, 61 on bottom not shown) at the top and the bottom of expansion member 50. Lateral connectors 60 and 61 connect blades 62 and 64 at a location along the length of the blades between proximal end 52 and distal end 54 of expansion member 50, at a location that is approximately mid-way along the length of the blades. Connectors 60 and 61 can be referred to as double-pivot type connectors because each connector connects to both blades, and each connection between the connector and the blade includes a pivoting hinge or joint. More specifically, each connector 60 and 61 has two opposite ends (60a, 60b, 61a, and 61b) and a length therebetween. Each end of each connector is connected to a blade at a pivoting hinge that allows each blade to rotate about each end of connectors 60 and 61.

Blades 62 and 64 are connected at connectors 60 and 61, allowing a user to move handles 55 and 56 toward and away from each other, whereby a distance (width 74) between blades 62 and 64 at a location at distal end 54 becomes larger and smaller, respectively (the blades at the distal end will move in opposite directions compared to the handles). In use, such as in a transvaginal procedure to access tissue in a region of a sacrum, a surgeon is able to insert expansion member 50 transvaginally with the space between opposing blades 62 and 64 at distal end 54 in a closed configuration, with little or no space or distance between the distal ends of the opposing blades (e.g., width 74 is zero or relatively small). Proximal end 52 remains external to the patient and distal end 54 passes transvaginally to a location at a posterior pelvic region, e.g., at a surgical location of a region of sacral anatomy. During or after insertion, distal end 54 can be opened and closed as desired by closing or spreading (respectively) handles 66 and 68 to cause movement of the distal ends of blades 62 and 64 away from or toward each other, with the blades moving in a pivoting motion about the ends of connectors 60 and 61. Moving handles 55 and 56 closer together will increase the distance or width 74 between the distal ends of blades 62 and 64, and spreading handles 55 and 56 farther apart will decrease width 74. After the surgical procedure is completed, expansion member 50 can be removed from the patient.

Expansion member 50 of FIG. 2B is of a similar design but with a different variation of connector, and can function in the same manner as expansion member 50 of FIG. 2A. Referring to FIG. 2B, expansion member 50 includes connectors 65 and 66 at the top and the bottom of expansion member 50. Connectors 65 and 66 connect blades 62 and 64 at a location along the length of the blades between the proximal and the distal ends of the blades, at a location that is approximately at mid-way along the length of the blades. Connectors 65 and 66 can be referred to as single-pivot type connectors because each connector and each connection between the blades includes a single pivoting hinge (68). More specifically, each connector 65 and 66 has two ends (65*a*, 65*b*, 66*a*, and 66*b*, the latter two being not shown) and a length therebetween. Each end (65*a*, 65*b*, 66*a*, and 66*b*) is connected to a blade at a non-pivoting connection, and each connector (65, 66) includes a single hinge (68) (as illustrated, located about mid-way between the blades).

Figure 3A:
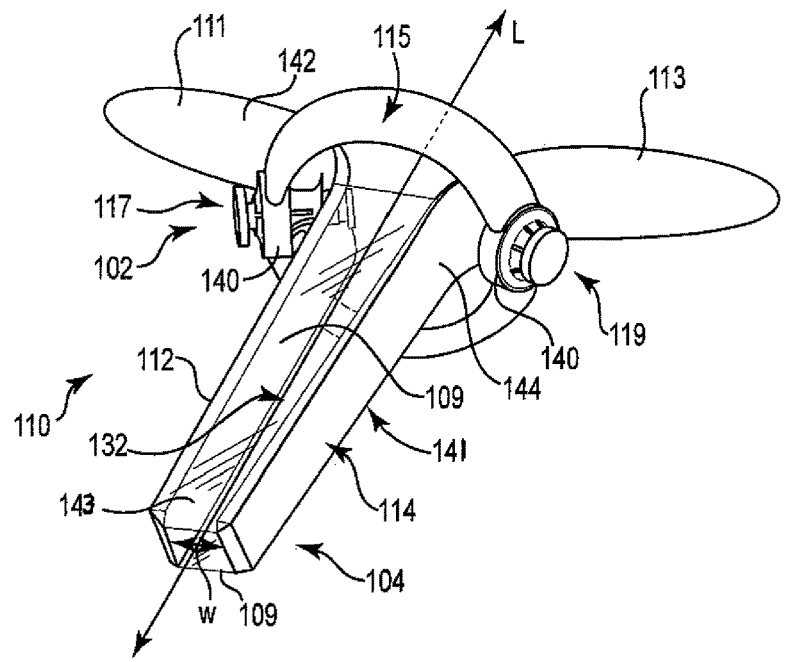
FIGS. 3A and 3B are side perspective views of an embodiment of an expansion member.
Figure 3B:
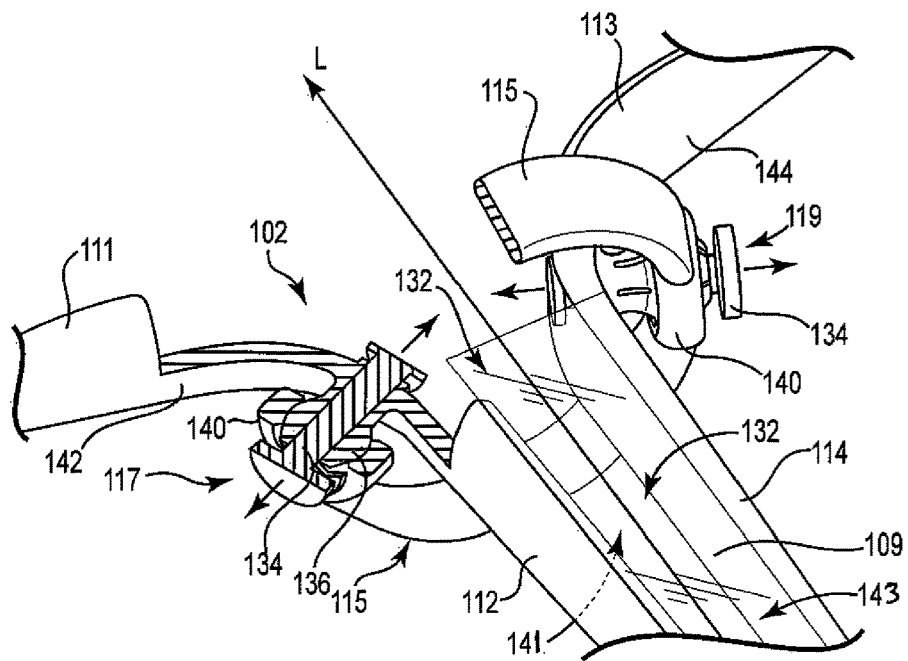

Referring to FIGS. 3A and 3B, retractor or expansion member 110 includes proximal end 102, distal end 104, longitudinal blades 112 and 114, handles 111 and 113, frame 115, and locking joints or hinges 117 and 119. Expansion member 110 is configured for use during a surgical procedure to provide access to a surgical site or anatomy, e.g. transvaginal access to a region of sacral anatomy.

Frame 115 connects to assemblies 142 and 144, each including a blade (112, 114) and a handle (111, 113), at proximal end 102, through locking joints 117 and 119. As shown, frame 115 is circular, but other shapes (e.g., oval, square, rectangular) could also be useful. Locking joints 117 and 119 include two circular collars 140 that are fixed to frame 150 at locations on opposite sides of frame 115, fixing the locations of the blade and handle assemblies 142 and 144 about the circumference of frame 115.

Locking joints 117 and 119 can be unlocked to allow movement between an assembly (142, 144) and the frame, or locked to prevent such movement. Each joint 117 and 119 includes collar 140 including an aperture, expandable ball 136 within the aperture, and tapered pin 134. Tapered pin 134 is slidable between positions within expandable ball 136, and expandable ball 136 is positioned within an aperture of circular collar 140. Tapered pin 134 includes a wide end and a narrow end. Expandable ball 136 can be expanded (to lock the joint) and contracted (to unlock the joint) by movement of tapered pin 134 between extended and retracted positions (see arrows at FIG. 3B). Movement of tapered pin 134 will expand or contract the size of ball 136, causing ball 136 to engage or disengage an interior surface of the aperture of collar 140. When the narrow end of tapered pin is located within ball 136, ball 136 is contracted, the joint (117, 119) is unlocked, and a blade and handle assembly (142, 144) can be moved relative to frame 115 by pivoting (universally) about ball hinge 117, 119. When the wide end of tapered pin is located within ball 136, ball 136 is expanded, the joint (117, 119) is locked, and each blade and handle assembly (142, 144) is fixed in position in a manner sufficiently secure to allow blades 112 and 114 to hold retracted tissue in place.

Still referring to FIGS. 3A and 3B, expansion member 110 is configured for use during a surgical procedure to provide access to a surgical site or anatomy, e.g., transvaginal access to a region of sacral anatomy. Blade 112 is a side blade having a straight cross-sectional profile along a length between a proximal end (at the handles) and a distal end. Blade 114 is a side blade having a straight cross-sectional profile along a length between a proximal end (at the handles) and a distal end. Access space 132 is the longitudinal interior space between blades 112 and 114, including longitudinal axis "L." Optionally and as illustrated, expansion member 110 includes top and bottom longitudinal openings (slots, or channels) 141 and 143 extending longitudinally along the length of expansion member 110 between opposing top and bottom edges of blades 112 and 114. As illustrated, flexible film (or membrane) 109 is placed to span or cover each of openings 141 and 143. Width W is measured between distal ends of blades 112 and 114 at a location at the distal end (e.g., as shown at FIGS. 3A and 3B). Width W can be increased or decreased by movement of handles 111 and 113.

Blades 112 and 114 are lockably connected to frame 115 at lockable joints 117 and 119. When joints 117 and 119 are unlocked, a user can move handles 111 and 113 toward and away from each other, whereby a distance (width, W) between blades 112 and 114 at a location at distal end 104 will become larger and smaller, respectively (the blades at the distal end will move in opposite directions compared to the handles). In use, such as in a transvaginal procedure to access tissue in a region of a sacrum, a surgeon is able to insert expansion member 110 transvaginally with the space between opposing blades 112 and 114 at distal end 104 in a closed configuration, with little or no space between the distal ends of the opposing blades (e.g., width W is zero, or relatively small). Proximal end 102 remains external to the patient and distal end 104 passes transvaginally to a location at a posterior pelvic region, e.g., at a surgical location of a region of sacral anatomy. During or after insertion, distal end 104 can be opened and closed as desired by closing or spreading (respectively) handles 111 and 113 to cause movement of the distal ends of blades 112 and 114 away from or toward each other, with the blades moving in a pivoting motion about joints 117 and 119. Moving handles 111 and 113 closer together will increase the width W between the distal ends of blades 112 and 114, and spreading handles 111 and 113 farther apart will decrease width W. The ability to move the blades independently improves the ability to navigate the distal end through posterior pelvic tissue including the bowel. Alternating back and forth, one blade can be used to hold tissue while the second blade sweeps tissue aside. The membrane or film (109) provide top and bottom surfaces that prevent bowel from encroaching between the blades. When a sacral promontory is reached and cleared of bowel, the blades are locked in position to provide a stable access space through which to complete the surgical procedure. After the surgical procedure is completed, expansion member 50 can be removed from the patient.

Figure 5:
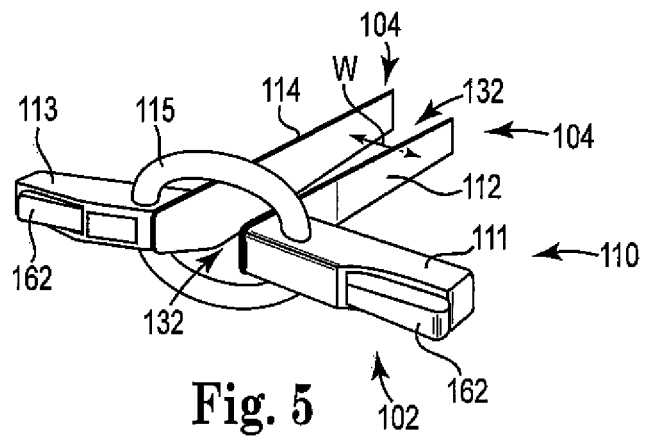
FIG. 5 is a top perspective view of an expansion member of the invention.
Figure 6A:
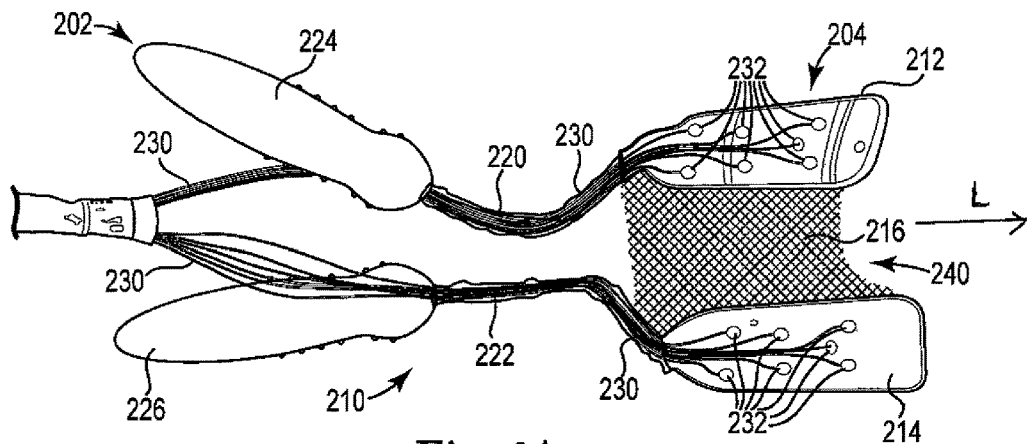
FIG. 6A is a top view of an expansion member of the invention.
Figure 6B:
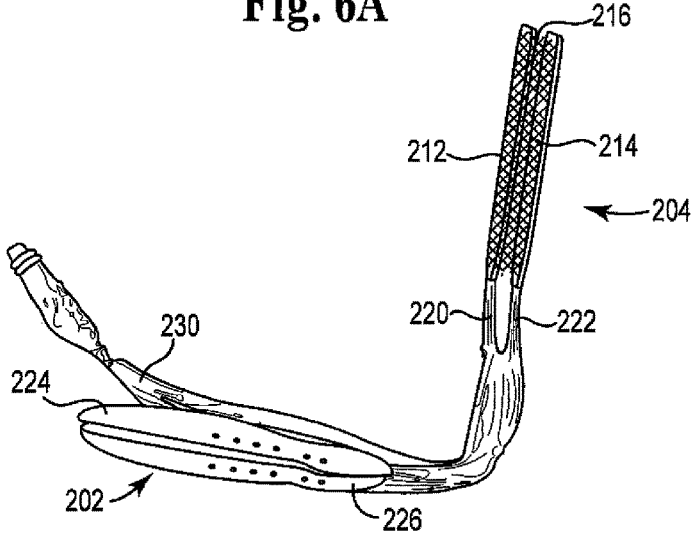
FIG. 6B is a side view of an expansion member of the invention.
Figure 6C:
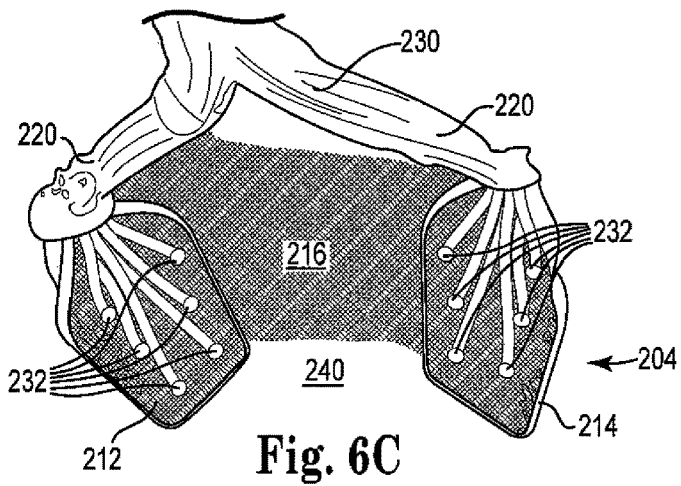
FIG. 6C is a bottom view of a distal end of an expansion member of the invention.
Figure 6D:
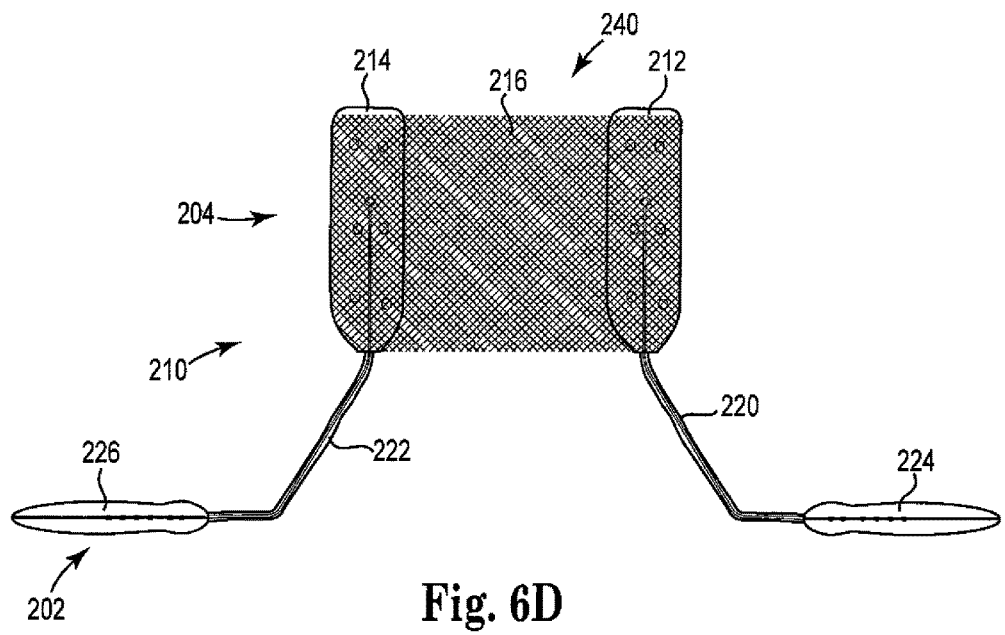
FIGS. 6D and 6E are top views of an expansion member of the invention.
Figure 6E:
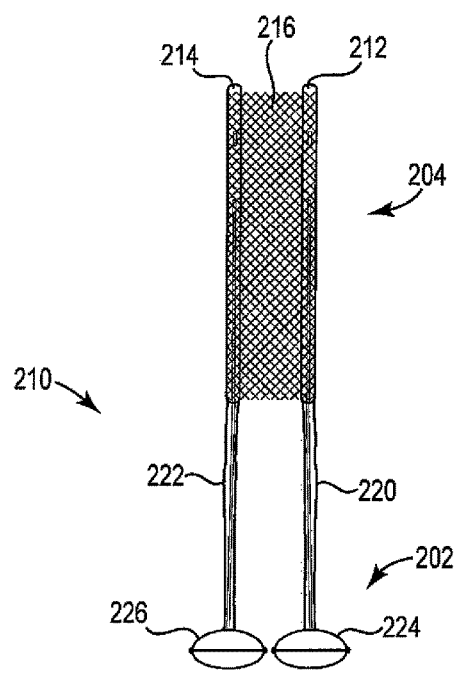

FIG. 5 shows an alternate version of expansion member 110, which can be used in a manner similar to expansion member 102 of FIGS. 3A and 3B, and which includes alternate versions of handles 111 and 113. Expansion member 110 also includes a rectangular or oval frame 115, and does not include flexible films 109 spanning the top and bottom edges of blades 112 and 114. See FIG. 5.

Figure 4A:
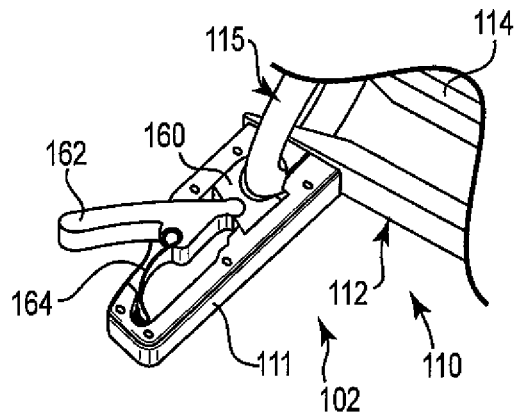
FIGS. 4A and 4B are cut-away side perspective views of handles of an embodiment of an expansion member.
Figure 4B:
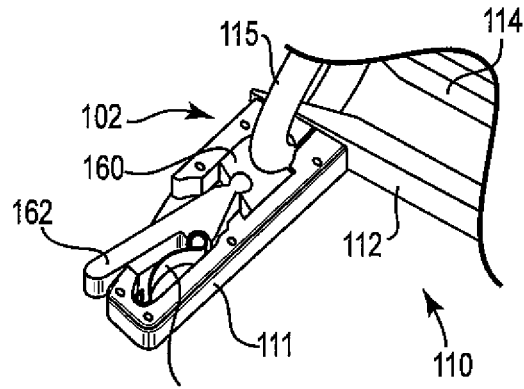

As shown at FIGS. 4A and 4B, handles 111 (and 113, not shown) include an alternate version of a lockable joint. Handle 111 includes block 160, which can alternately be moved against or away from frame 115 by movement of lever 162. Spring 164 is biased to hold lever 162 in an unlocked position, with block 160 disengaged from a surface of frame 115. See FIG. 4A. To lock handle 111 in place, lever 162 is pushed toward handle 111 (see FIG. 4B) causing block 160 to contact frame 115 and secure handle 111 and blade 112 in place for use in a surgical procedure. A detent, latch, spring-biased pin engagement, or other frictional or mechanical mechanism can maintain handle 111 in the locked position for using expansion member 110 during a surgical procedure. Afterward, handle 111 can be manually moved to an unlocked position. To provide desired friction between block 160 and frame 115, opposing surfaces may be structured to include teeth, knurling, etc.

Referring to FIGS. 6A, 6B, 6C, 6D, and 6E, retractor or expansion member 210, including proximal end 202, distal end 204, two longitudinal blades (or paddles) 212 and 214, connector (connective mesh) 216, shafts 220 and 222, and handles 224 and 226. Optical fibers 230 extend in a proximal direction to a light source (not shown), and distally along shafts 220 and 220, to paddles 212 and 214, where terminal ends 232 of optical fibers 230 are located to illuminate an access space 240 located between blades 212 and 214.

Expansion member 210 is configured for use during a surgical procedure to provide access to a surgical site or anatomy, e.g. transvaginal access to a region of sacral anatomy. Blade 212 has a straight cross-sectional profile between a distal and a proximal end (alternately, blade 212 could include a curved cross-sectional profile along a portion or all of the length of the blade). Blade 214 has a straight cross-sectional profile between a distal and a proximal end (alternately, blade 214 could include a curved cross-sectional profile along a portion or all of the length of the blade). Blades 212 and 214 are connected between longitudinal edges of each blade by a flexible film or mesh connector 216. As illustrated, connector 216 is a woven, knit, or otherwise porous film or mesh prepared from strands of polymeric material such as polypropylene (alternately another polyolefin or other polymeric strand material, or a continuous or porous film). Connector 216 connects blades 212 and 214 while allowing movement of blades 212 and 214 between a closed configuration and an open configuration. In a closed configuration, shown at FIGS. 6B and 6E, blades 212 and 214 are closely spaced, as are handles 224 and 226. In an open configuration, shown at FIGS. 6A, 6C, and 6D, blades 212 and 214 are spaced apart from each other to extend connector 216 and to create access space 240 between blades 212 and 214, and connector 216; handles 224 and 226 are also spread apart. Access space 240 is the access space between blades 212 and 214 and connector 216, including a longitudinal axis (L) between the blades and the connector. A size (e.g., width) of the access space between the blades will increase and decrease as the blades are spread apart and moved together, respectively, creating a larger or smaller access space 240.

Blades 212 and 214 are connected at connector 216, and also to shafts 220, 222, and handles 224 and 226. The arrangement allows a user to move handles 224 and 226 as desired, including laterally closer or farther apart, or distally toward and away from each other. A distance between blades 212 and 214 at a location at distal end 204, and an access space between the blades, can be made larger and smaller, respectively. In use, such as in a transvaginal procedure to access tissue in a region of a sacrum, a surgeon is able to insert distal end 204 of expansion member 210 transvaginally with opposing blades 212 and 214 at distal end 204 in a closed configuration, with little space between the opposing blades. Proximal end 202 remains external to the patient and distal end 204 passes transvaginally to a location at a posterior pelvic region, e.g., at a surgical location of a region of sacral anatomy. During or after insertion, blades 212 and 214 at distal end 204 can be spread apart by spreading handles 224 and 226 to cause movement of the blades 212 and 214 away from each other, and causing connector 216 to spread and push back adjacent tissue. Spreading handles 224 and 226 apart will increase the distance (width) between blades 212 and 214, and moving handles 224 and 226 closer together will decrease that distance (width). During the procedure, paddles and connector 216 can create an access space at posterior pelvic region, keeping adjacent tissue out of the access space. Lighting (230 and 232) can be used to illuminate the access space during a surgical procedure. After the surgical procedure is completed, expansion member 210 can be removed from the patient.

Alternate embodiments of devices useful in a manner similar to expansion members as described are also contemplated for use in providing access to internal tissue of a pelvic region through an incision in a male or female patient, e.g., as a tissue retractor used to gain transvaginal access to a posterior region of a female pelvic anatomy. Any of the generally or specifically described expansion members may be useful according to one or more of the methods described herein for placing an implant to support pelvic tissue, for example a SCP procedure, using any one or more of the herein-described implants, insertions tools, multi-functional tools, anchors, etc.

Various such embodiments of "expansion members" are described herein and may have general structural and operational features that allow one or more flexible, rigid, or semi-rigid, distal retracting structures to be introduced through an incision (e.g., a vaginal incision) in a closed, compressed, or reduced-size or reduced-diameter state, then the moved, assembled, or expanded to enlarge a cross-sectional size or related space or opening to push tissue aside to create space in and access to a pelvic region with access to desired pelvic anatomy. A preferred size of a device can include a cross sectional dimension (e.g., a width or diameter associated with an opening along a length of the device) in the range from 1 to 5 centimeters, such as from 2 to 4 centimeters, when distal retracting structures are in their the reduced-size configuration. Upon opening, un-compressing, expanding, or assembling, etc., the distal retracting structures, a preferred dimension (e.g., a width or diameter associated with an opening along a length of the device) associated with these structures can be in the range from 2 to 10 centimeters, such as from 3 to 7 centimeters. Also generally, these structures (retractors and the like) can include desired length dimensions (from a proximal to a distal end) that can be selected to work with a particular anatomy (male or female) and procedure (anterior repair, posterior repair, etc.). A length of a specific structure (tube, retractor, etc.) useful in a transvaginal method of treating a posterior pelvic condition (e.g., a SCP procedure) can be sufficient to allow the distal end to reach a region of a sacral anatomy as a proximal end remains at or outside of the vaginal introitus. A related dimension is the "working depth" of such a device, which is the distance between the distal end of the device and the vaginal introitus, when installed, and which can be any dimension useful or desired, e.g., from 13 to 18 centimeters. A distance by which the device extends proximally, away from a patient, out of the vaginal introitus, is preferably minimized. Still referring to the use of these devices in transvaginal methods of treatment, another relevant dimension is a "working space" dimension, which is a lateral dimension of an opening at a proximal end of the device, such as a diameter, which may preferably be in a range from 3 to 8 centimeters; in a transvaginal method, this is an approximate diameter of a vaginal introitus held open by a proximal end of the device.

According to exemplary uses of certain described expansion members, including any optional features alone or in combination, a vaginal process to reach a sacral promontory can include:
1—Complete an incision through the vaginal apex (or posterior to the apex) and the peritoneum;
2—Confirm sacral promontory (bone=firm feel, promontory=increased depth with minimal anterior movement);
3—Place the expansion member through the vaginal introitus, through the incision, and advance until the distal edge (e.g., the tip of the distal end) meets the sacrum;
4—Open the expansion member (e.g., at the distal end);
5—Optionally, connect a light source (if an external source is used);
6—A working space to the sacrum has been opened and is lighted.

Also according to embodiments of the methods, implants, tools, and devices described herein, any of the described tools can be used for placing any desired pelvic implant in a male or a female patient, and for any of a large variety of conditions, such as a pelvic condition. The implant can include any structural features useful for such treatment, including any desired size, shape, and optional features such as adjustability and anchoring systems. Any of these features may be previously known, future developed, described herein, or described in documents incorporated herein, for any particular implant and method. For example, some figures and discussions include examples of features of "anchors" (e.g., soft tissue or bone anchors, as these terms are generically and inclusively used) that can be useful according to the methods of placing a surgical implant. An implant that includes or is otherwise secured by any of the anchors described can be useful to treat a pelvic condition in a male or a female patient; as a single and non-limiting example, an implant that includes or uses an anchor as described can be used in a transvaginal SCP procedure to provide support to a vaginal cuff, through an implant that includes the anchor, the anchor being attached at a region of sacral anatomy such as a sacral ligament (e.g., anterior longitudinal ligament, a.k.a. the "anterior ligament" or "longitudinal ligament").

Various devices and methods described herein are advantageous because they facilitate reduction of total procedural time if the patient needs a urinary sling, levator floor support, high apical support (fixation to the sacrum), and anterior or posterior prolapse by combining multiple products into one. The pelvic floor support reduces the long term prolapse recurrence as well as improve the patient's sexual function with the high apical support due to the sacral fixation. Moreover, the various tools and methods allow a physician to use a transvaginal approach and achieve a similar tension as what is currently only achievable in a abdominal or laparoscopic approach to the sacrocolpopexy procedure.

The various systems, apparatus, and methods detailed herein are envisioned for use with many known implant and repair systems (e.g., for male and female), features and methods, including those disclosed in U.S. Pat. Nos. 7,500, 945, 7,407,480, 7,351,197, 7,347,812, 7,303,525, 7,025,063, 6,691,711, 6,648,921, and 6,612,977, International Patent Publication Nos. WO 2008/057261, WO 2007/097994, WO 2007/149348, and U.S. Patent Publication Nos. 2002/151762, 2010-0174134, 2010-0298630, 2002/147382, and WO 2011/082350 A1, published 7 Jul. 2011. Accordingly, the above-identified disclosures are fully incorporated herein by reference in their entirety.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:
1. An expansion member comprising:
a proximal end, a distal end, and a length extending from the proximal end to the distal end,
a first assembly comprising a first handle at the proximal end, and a first longitudinal blade extending distally in a length direction at the distal end, the first longitudinal blade having first and second longitudinally-extending edges and a first shaft connecting the first handle to the first longitudinal blade, wherein the first shaft and the first longitudinal blade are adapted to allow the expansion member to be used by passing a distal end of the first longitudinal blade through a vaginal introitus to extend the distal end of the longitudinal blade to a region of posterior pelvic tissue, the first longitudinal blade being planar between a distal end of the first longitudinal blade and a proximal end of the first longitudinal blade,
a second assembly comprising a second handle at the proximal end, and a second longitudinal blade extending distally in a length direction at the distal end, the second longitudinal blade having first and second longitudinally-extending edges and a second shaft connecting the second handle to the second longitudinal blade, the second assembly being moveable in three dimensions relative to the first assembly, wherein the second shaft and the second longitudinal blade are adapted to allow the expansion member to be used by passing a distal end of the second longitudinal blade through the vaginal introitus to extend the distal end of the second longitudinal blade to the region of posterior pelvic tissue, and wherein the second handle is disconnected from the first handle, a connector at the distal end, coupled to the first edge of the first longitudinal blade and the first edge of the second longitudinal blade, the connector including a flexible mesh sheet defining a plurality of pores, wherein the connector is not coupled to the second edge of the first longitudinal blade, and the connector is not coupled to the second edge of the second longitudinal blade, the connector allowing movement of the first longitudinal blade relative to the second longitudinal blade to increase a distance between the first blade and the second blade at the distal end to form an open configuration and to subsequently decrease a distance between the first blade and the second blade at the distal end to form a closed configuration, a plurality of first optical fibers coupled to a common light source, the plurality of first optical fibers extending along the first shaft, the plurality of first optical fibers having a plurality of first terminal ends disposed on different locations on the first longitudinal blade, and a plurality of second optical fibers coupled to the common light source, the plurality of second optical fibers extending along the second shaft, the plurality of second optical fibers having a plurality of second terminal ends disposed on different locations on the second longitudinal blade.

2. The expansion member according to claim 1, wherein the first longitudinal blade is configured to move in three dimensions relative to the second longitudinal blade by manipulation of the first handle and the second handle.

3. The expansion member according to claim 1, wherein the first handle is configured to be manipulated in three dimensions relative to the second handle, to move the first longitudinal blade and the second longitudinal blade between the open configuration and the closed configuration.

4. The expansion member as recited at claim 1, further comprising a distal edge that is angled relative to a longitudinal axis, when viewed from a side.

5. A method of transvaginally performing pelvic surgery to support a vaginal apex, the method comprising:
providing the expansion member according to claim 1,
making an incision in a patient,
inserting the distal end through the incision,
using the expansion member to provide access to a region of sacral anatomy.

6. The method according to claim 5, further comprising:
while the expansion member is placed through the incision, increasing a size of an access space of the expansion member.

7. The method according to claim 5, wherein the incision is a vaginal incision and the method comprises inserting the distal end through the vaginal introitus and through the vaginal incision.

8. The method according to claim 5, comprising:
while the expansion member is placed through the vaginal introitus, increasing a size of an access space between the first longitudinal blade and the second longitudinal blade of the expansion member.

9. The method according to claim 5, wherein the expansion member is adapted to provide surgical access to a vaginal apex.

10. The expansion member according to claim 1, wherein the connector extends only between a portion of a length of the first longitudinal blade and a portion of a length of the second longitudinal blade.

11. The expansion member according to claim 1, wherein the first longitudinal blade and second longitudinal blade are configured to be inserted into an incision in the closed configuration, opened into the open configuration during a surgical procedure, and then re-closed to be removed while in the closed configuration.

12. The expansion member according to claim 1, wherein in the open configuration, an access space is formed between the first longitudinal blade, the second longitudinal blade, and the connector, the access space including an opening on a side of the access space along a length of the expansion member.

13. The expansion member of claim 12, wherein the opening is a slot or a channel extending along the length of the expansion member.

14. The expansion member of claim 12, wherein the opening extends lengthwise along lengths of the first longitudinal blade and the second longitudinal blade.

15. The expansion member according to claim 1, wherein the first longitudinal blade has a length that is greater in dimension than a width of the first longitudinal blade, and the second longitudinal blade has a length that is greater in dimension than a width of the second longitudinal blade.

16. The expansion member according to claim 1, wherein the first longitudinal blade extends distally in a substantially straight direction, and the second longitudinal blade extends distally in a substantially straight direction.

17. The expansion member according to claim 1, wherein the second longitudinal blade is planar between a distal terminal end of the second longitudinal blade and a proximal terminal end of the second longitudinal blade.

* * * * *